United States Patent [19]

Joyce

[11] Patent Number: 4,558,690

[45] Date of Patent: Dec. 17, 1985

[54] METHOD OF ADMINISTRATION OF CHEMOTHERAPY TO TUMORS

[75] Inventor: Patrick J. Joyce, Arlington, Va.

[73] Assignee: University of Scranton, Scranton, Pa.

[21] Appl. No.: 343,011

[22] Filed: Jan. 26, 1982

[51] Int. Cl.⁴ .................... A61B 19/00; A61M 5/00
[52] U.S. Cl. ................................. 128/1 R; 128/804;
  604/891; 604/20; 424/32; 424/78; 424/81
[58] Field of Search .............. 128/1.3, 1.5, 804, 1 R;
  604/20, 21, 890, 891; 424/32, 33, 78, 81

[56] References Cited

U.S. PATENT DOCUMENTS

| | | | |
|---|---|---|---|
| 3,991,770 | 11/1976 | LeVeen | 128/804 |
| 4,106,488 | 8/1978 | Gordon | 128/1 R |
| 4,269,826 | 5/1981 | Zimmerman et al. | 128/1.3 X |
| 4,323,056 | 4/1982 | Borrelli et al. | 128/804 X |
| 4,331,654 | 5/1982 | Morris | 128/1.3 X |
| 4,337,760 | 7/1982 | Rubin | 128/804 X |
| 4,345,588 | 8/1982 | Widder et al. | 128/1.3 |
| 4,359,453 | 11/1982 | Gordon | 128/1.3 X |

OTHER PUBLICATIONS

Johnson et al., "Thermal Enhancement of . . . Cytotoxicity", J. Nat. Cancer Inst., vol. 56, No. 4, Apr. 1973.

*Primary Examiner*—Lee S. Cohen

[57] ABSTRACT

An improved method of administration of microspheres of cytotoxic chemicals to tumor sites without effect on non tumor tissue is disclosed. The method comprises injection of chemotherapeutic agents coated with a thermoplastic polymer having a melting point above normal body temperature (in a melting point range of about 40°–46° C.) accompanied by dielectric radio-frequency localized heating of the tumor to elevate its interior temperature above the melting point of the encapsulating thermoplastic polymer. The tumor is partially necrosed and sensitized by the R.F. nonionizing radiation bombardment and the entry of the chemotherapy agent triggered by the removal of the protective coat of thermoplastic polymer.

A preferred embodiment of the invention is a dose of 30 mg of methotrexate (A-methopterin) in the form of spherical microscapsules having an average of 200–800 microns diameter and a polymer of polystearyl acrylate encapsulating coating of an average thickness of 1–50 microns. This dose is injected into the tumor and released by a 30–60 minute irradiation of the tumor by 175–200 watts of R.F. non-ionizing radiation at a frequency of 13.56 megahertz from a set of capacitive plates positioned on opposite sides of the impregnated tumors. The tumor temperature is elevated to a threshold temperature of 43° C. which is the melting point and release point of the encapsulated acrylic resin. The temperature of the rest of the organism outside the tumor remains at 39°–40° C. which is below the release temperature of the resin.

9 Claims, No Drawings

METHOD OF ADMINISTRATION OF CHEMOTHERAPY TO TUMORS

BACKGROUND OF THE INVENTION

At the present time the progress of chemical attack on neoplasms is hindered by the inability of the therapist to deliver the cytotoxic dose to the tumor without exerting deleterious side effects such as nausea, leukepenia, thromocytopenia, diarrhea, alopecia, cirrhosis, chills and fever, ulcerative stomatitis and the like on the rest of the patient's body.

The current methods of administration of most of the available chemotherapy in use today are either oral injestion of the drug which is absorbed in the gastro intestinal tract and transported by the systemic circulation to the site of the tumor or by injection. If the drug is injected it is either by intravenous or intramuscular injection closer into the location of the neoplasm. Nevertheless the chemical agent is made available to the general blood circulation running to numerous systems and organs other than the diseased tissue. Frequently the therapeutic dose range required to necrose the tumor has harsh cytotoxic effect on the immune system of the organism at a time when the cooperation of the host defense mechanism should be brought to bear to arrest the spread of metastasis of the cancer.

Presently no known manner of direct therapeutic delivery of the many known cytotoxic agents to the tumor has been successfully implemented in part because heretofore no viable means of dissimination of the drug throughout the tissue of the neoplasm was known and in part because no means of "inerting" the cytotoxic agent until it had reached its tumor target had been disclosed. Recently considerable experimental therapy of tumors has involved radio-frequency heating of tumor masses to elevate the temperature of the tumor to levels of 41° C. to as high as 50° C. It has been demonstrated many times that localized hyperthermia, as it is so generally termed by oncology, can be achieved while the temperature of the surrounding normal non neoplastic tissue can be maintained at normal body temperature of 37.5° C. or slightly higher in some cases but usually not over 40° C. An interesting fact found from this clinical research is that the so heated tumor tissue appears to be rendered more sensitive to attack by antimetabolites such as methotrexate which interfere with the internal metabolism of the tumor cells and their DNA replication. Ruptured cell structures and partially necrosed tumor tissue enhances the dessimination of cytotoxic agents if these chemicals can be safely introduced.

What has been lacking in the art is a means of delivery of a cytotoxic agent direct to this sensitized tumor mass which will not permit attack by the cell killer or antimetabolite until it reaches its destination at the tumor tissue. This means is now available and is the subject of the present innovative method sought to be patented.

PRIOR PATENTS IN THE FIELD OF THE INVENTION

The closest anyone has come to my concept of cytotoxic drug delivery is described in several patents by Edward Merrill the first issued in 1971 bearing U.S. Pat. No. 3,608,549 and a second patent in 1972 bearing U.S. Pat. No. 3,659,600. The first Merrill patent suggests emplanting a capsule containing testosterone in the neck of dairy cattle to give sustained release of a steroid in response to electrical current applied from an induction coil collar placed around the neck of the cow to generate inductive heating. Sustained release is the object here not avoidance of side effects since testosterone is not toxic to cows and is intended to be placed in the systemic circulation. The capsule wall of Merrill is formed of a polymer (silicone rubber) which does not melt in an induction field and maintains the capsule intact for administration of sustained medication.

The second later issued patent of Merrill teaches a drug permeable wall in a capsule which wall responds to an external magnetic signal to release estrogens from a capsule implanted under the skin. A second magnetic signal shuts off this flow of estrogen from the capsule.

U.S. Pat. No. 3,118,439. to Perrenound discloses melting of a Teflon coating on a segment of an implanted capsule to release a drug under the influence of a 2.0 megahertz R.F. field. This concept again deals with sustained release of non toxic drugs and the use and absorption of the drug is not limited to any particular growth or tissue in the body.

In 1976 a patent issued to LeVeen bearing U.S. Pat. No. 3,991,770 and disclosing a diathermic method of elevating tumor temperature to partially necrose the same. This patent while not intending to do so provided disclosure of a so called "trigger" which could be used to both sensitize the tumor tissue prior to introduction therein of polymer encapsulated microspheres of cytotoxic agents and at a selected time and place release the contents of those microspheres. This release of course is from the encapsulating polymer coating which renders them innocous to all tissue except that tissue having a surrounding temperature which either equals or exceeds the melting point of their encapsulating resin.

Hence the stage is now set for the beginning of a new era in drug therapy for tumors and perhaps other medications as well on the basis of thermal differentiation of tissue heat induced by externally applied tissue hyperthermia. These objects and others will become obvious to those skilled in the art as one reads the following details of my invention.

OBJECTS OF THE INVENTION

It is a primary process object of the present invention to disclose a means of administration of tumoricidal agents directly into tumors without wide effect on healthy tissue outside the tumor mass.

It is a product object of the invention to disclose a new dosage form of a lethal encapsulated cytotoxic chemical which is biologically inert at environmental temperature below the melting point of the encapsulating coating but biologically active at temperatures in its environs above that level.

It is a process object to disclose a new method for activating a coated chemical agent by encapsulating same with a releaseable inert coating and removing that coating by means of a radio signal transmitted to the microsphere itself and its surrounding environment.

THE INVENTION

Accordingly the present invention comprises a new means of administration of cytotoxic chemicals to tumors to necrose the same while at the same time sparing the rest of the body of the patient from the lethal effects of the cytotoxic substances.

As an integral part of that method of administration a new microsphere dosage unit is disclosed which is particulate in nature has either a solid or liquid core a diameter of from about 200–800μ and has a removable polymeric encapsulating coating of 1–50μ thickness which will melt at a temperature of 40°–46° C. and more specifically at a temperature of 43° C. when heated at that temperature for at least 10 minutes.

The contents of the microcapsule can be any liquid or solid medicament but for purposes of the limited oncology application the invention will be discussed with reference to solid and liquid tumoricidal agents. Such known agents as the well known antimetabolites methotrexate or cytoxan may be employed. These chemicals are the type of cell killers which are currently being employed to halt the proliferation of the abnormal tumor cells but because of their general cytotoxic behavior cannot be restricted in their attack to diseased tissue alone at the present time.

The particulate microsphere has a unique character type coating which is a thermoplastic polymer which melts in response to diathermic heat to release the trapped contents of the microcapsule to the tissue environment where it is located at the time the encapsulating resin is melted away. A preferred type of such coating is a 1–50μ coating of polystearyl acrylate which melts at a temperature of 43° C. to dissolve away and disgorge its contents to its surroundings at the time of release. At any temperature lower than 43° C. the coating is biologically inert and will not release its contents until this temperature is attained.

The encapsulating coating of polymer covering the microsphere must be compatible with the chemical contents of the microsphere as well as being biologically inert to the body tissue through which it must pass. The thin coating must nonetheless be capable of withstanding reasonable fracture until it is melted and removed. Finally and most importantly the coating must be capable of being diathermically heated to its melting point by known and available R.F. diathermy apparatus such as that described in U.S. Pat. No. 3,991,770.

Any of several well known methods can be used to apply the acrylic capsule wall coating to the methotrexate. Some examples of known and eligible capsule wall coating methods include pan coating wherein a solution of the capsule wall material is sprayed onto internal phase particles of drug which are tumbling in a rotating bowl; impingement coating wherein the internal phase particles i.e. methotrexate are impinged onto and cast through a liquid film of the capsule wall polymer material and thereby to become coated with the encapsulating resin material. Finally the encapsulation by the liquid phase separation of the capsule wall polymer material wherein the internal phase particles are distributed in a two phase liquid capsule manufacturing system consisting of a phase of continuous suspending liquid and a phase of dispersed liquid droplets of the capsule wall material which droplets coat the internal phase particles to yield capsules.

Various prior art publications have reviewed methods of microencapsulation by phase separation and these include:

1. U.S. Pat. Nos. 4,166,800, 3,608,549 and 3,909,444 whose text is incorporated by reference herein.
2. The technical publication entitled "Microencapsulation" by Louis A. Luzzi in the Journal of Pharmaceutical Sciences, Vol. 59 No. 10, pp. 1367–1376 (1970)
3. "Microencapsulation" by Wolfgang Sliwka in Chem. Internat. Edit. Vol 14, No. 8, pp. 539–550 (1975)
4. "A Review of Microencapsulation" by Nawal N. Salib in Pharm. Ind. Vol 39 No. 5, pp. 506–512 (1977)
5. Microencapsulation, Processes and Applications edited by Jon F. Vandegner, Plenum Press, N.Y. (1974) and
6. Microencapsulation—edited by J. R. Nixon Marcel Dekker Ind N.Y. (1976) all of which are herein incorporated by reference to teach the reader how to make microspheres.

While the product aspect of the invention relates to thermally responsive encapsulated microspheres the process aspect involves a method of treating tumors employing these new polymer encapsulated microspheres as a means of drug delivery of cytotoxic chemical to the tumor target without effect on other nontumor tissue.

Before the chemotherapeutic drug dose is delivered to the tumor the neoplasm should first be sensitized by irradiation of radiowave energy preferably at a frequency of 13.56 or 27.6 megahertz which are the medically approved F.C.C. bandwidths for hospital use in medical diathermy. Experience has demonstrated that bombardment of a tumor mass with between 175–200 R.F. watts at this frequency will elevate tumor temperature above 40° C. and up to as high as 46° C. after about 15 to 20 minutes of treatment. For therapy details reference is made to U.S. Pat. No. 3,991,770 whose disclosure is incorporated by reference here.

The internal tumor temperature is measured by an implanted Bailey thermocouple which is monitoring the tumor temperature, the peritumor temperature of the tissue just outside the tumor and the skin temperature simultaneously, all must be taken. When the tumor temperature peaks at just under the melt temperature of the encapsulating resin the dose of microcapsules in a suitable vehicle such as sesame seed oil is injected into the interstices of the neoplasm. This injection can be made in part or its entirety but preferable is fractionated into several aliquots spaced five minutes apart to allow time for the drug to become desseminated through the tumor. A large 18 or 20 gauge needle and 50 cc syringe is employed for this purpose.

As a practical matter the treating physician will in the case of lung or other submerged tumors have already located and marked the tumor target for implantation of the temperature recorder thermocouple or thermister. Once the dose of medicament has been placed in the tumor thermotherapy is continued for at least an additional 30–45 minutes to permit all of the antimetabolite cytotoxic agent to perfuse the neoplasm. Should any of the antimetabolite escape from the tumor for any reason it will pass into a low temperature peritumor temperature zone where it is inert because of its protective encapsulating coat of polymer.

Once the dosage by injection is commenced it is preferable to simply leave the delivery needle in place and attach thereto a filled syringe of a repeat dose of the chemotherapeutic agent or combination thereof selected by the treating physician. It is of course obvious that the concurrent R.F. thermotherapy and chemotherapy do not interfere with one another and may be conducted for as long as is deemed necessary by the treating physician. Furthermore the nature of this treatment has the advantage that systemic injection of immune stimulators may be carried on at the same time to enhance the body natural defense mechanism. Outside the tumor no cell necrosis since all of the cytotoxic impact of the killer chemicals are contained within the neoplasm leaving the phagocytic cells of the systemic circulation free to proliferate and control metastatic spread.

A number of currently available cancericidal chemical agents may be conveniently employed in the herein described method of treatment, in addition to the antimetabolite methotrexate which inhibits the reduction of folic acid and thus blocks cancer cell replication when administered in 15 to 30 milligram daily doses for about 5 days or a total maximum dose of about 150 milligrams, certain other cytotoxic agents may be also administered. Adriamycin given once every 21 days in adult doses of 60 mg/meter$^2$ of body surface intravenously now could be given intratumorally in the same quantity maintained in acrylic resin coated microcapsules having a coating of 10–50$\mu$ thickness and a particle size of 250 microns in diameter with a core width of about 200 microns.

The well known agent Bleomycin found to be useful in inhibition of the cell proliferation of squamous cell carcinoma of the head and neck when administered intravenously twice weekly in unit doses of 0.25 to 0.5 units per kilo of body weight of the subject (about 50 to 100 units for subject weighing between 100 and 200 pounds) can be coated with a 50$\mu$ coating of polystearyl acrylate of moderate molecular weight 20,000 to 100,000 units after being milled to a particle size of 250–500 microns diameter and injected in a liquid carrier such as physiologic saline or glucose and administered over a period of 10 to 20 minutes through a 15 gauge needle subcutaneously in the tumor mass.

Likewise cyclophosphamide (CYTOXAN) the well known alkylating agent may be encapsulated in a manner similar to Bleomycin and administered intratumorally in a dose of 40–60 mg/kilo of patient body weight daily dose for two to five days. This agent has a history of necrosis of adinocarcinoma of the ovary and occasionally is active against adinocarcinoma of the lung.

In a similar manner other known chemotherapeutic agents such as (p-di(2-chloroethyl) amino-L-phenylalanine); CYTOSAR(1-B-D-arabinofurano-sylcytosine); DICORVIN(diethylstilbesterol); DROLBAN (17 -hydroxy-2 -methyl -5 androstan-3-one) can be coated and applied.

The invention will be further elaborated by the following illustrative example of a preferred mode of preparation of the polymer encapsulated microspheres of the various chemotherapeutic agent enumerated hereinabove.

EXAMPLE

A solution of one gram of polystearyl acrylate in 50 ml of a toluene solvent can be cooled to about $-65°$ C. in a dry ice-isoproponal bath. Micronized methotrexate (0.5 gram) powder can be dispersed in the polymer solution with stirring at 160 RPM. Isopropanol (150 ml) can be added dropwise to the dispersion at the rate of one hour for the first 50 ml and one half hour for the remaining 100 ml. The dry ice bath can be removed and the microcapsules allowed to settle before decanting the supernatant. The product can be washed twice with heptane dried and weighed. Microscopic examination should disclose spherical microcapsules with a diameter of about 125–150 microns.

For controlled release of the drug suitable for parenteral or subtumoral administration the size of the microspheres should be large enough to provide adequate duration of release yet small enough to not restrict passage through the standard syringe needles employed. Thus the most desired particle size is about 150 microns for a No. 20 gauge syringe needle.

For other applications it may be desirable to allow formation of larger microspheres up to 250 or 300 microns in diameter.

However in the case of treatment of a 6 centimeter diameter squamous cell carcinoma of the neck for example one should inject 10 cc of polystearylacylate encapsulated (40 microns coating thickness) Bleomycin from a 50 cc hypodermic syringe which is fitted with a 20 gauge hypodermic needle. The tumor so treated will have been pre-heated to a median intratumoral temperature of 43°–45° C. by twenty minutes of R.F. 13.56 megahertz capacitive plate diathermic heating by emanation of from 175–200 R.F. watts from a TRIPORT 222 radiofrequency generator.

After the encapsulated drug has been completely infused into the tumor mass the heating will be continued for at least another 30 minutes with a second 10 cc aliquot of encapsulated cytotoxic agent being administered in the interim.

The patient will of course be monitored in a similar manner to other patients being given chemotherapy.

As well as the polystearyl acrylate encapsulating resin other thermoplastic moderate range melting encapsulating polymers which melt between the temperatures of 40 and about 46° C. may be employed to releasably coat the chemotherapeutic agents of the invention. Such material as polyheptadecyl acrylate, lauric acid, and esters of this acid such as glycerol trilaurate may also be employed in the practice of this invention. Actually any encapsulating material either monomeric or polymeric which is solid and inert at a normal body temperature range and melts at a range of 40°–50° C. can be employed so long as it is capable of being coated on the microparticles of medication to be introduced into the tumor.

By the use of the terms "polymeric coating" as employed in the several appended claims there is intended to embrace all encapsulating materials which are polymeric in nature and melt at a temperature higher than normal body temperature.

I claim as my invention:

1. A method for treatment of tumors of animals and humans which comprises:
   (a) elevating the temperature of the tumor with exposure to a nonionizing radiofrequency field to partially necrose and attenuate its cells,
   (b) injecting intratumorally and extracellularly into the tumor interstices a therapeutic dose of a tumoricidal agent encapsulated with a polymeric coating of a biologically inert thermoplastic resin characterized as having a melting point higher than the temperature of the surrounding body tissue and within the elevated temperature range of the tumor,
   (c) activating the tumoricidal agent by heating the same within the tumor interstices above the melting point of the encapsulating resin so as to release the same within the tumor interstices without exposing the remaining normal body tissue to the effects of the agent.

2. A method according to claim 1 wherein the tumoricidal agent employed has an encapsulating thermoplastic polymer coating which melts within a temperature range of 40°–46° C.

3. A method according to claim 2 wherein the tumoricidal agent encapsulated is methotrexate and the encapsulating thermoplastic polymer is an acrylate resin having a melting point of 43° C.

4. A method according to claim 3 wherein the encapsulating thermoplastic polymer employed is polystearyl acrylate.

5. A method for the administration of biologically active pharmaceuticals into a neoplasm of a mammal to reduce systemic side effects thereof which comprises:
   (a) introducing intratumorally and extracellularly into the interstices of the neoplasm within the segment of the mammal to be treated a therapeutic dose of microcapsules of a biologically active pharmaceutical which has been precoated with a releasable polymeric encapsulating resin coating which has a melting point range extending from 40°–46° C. and which until the coating is removed is substantially inert biologically,
   (b) removing this polymeric encapsulating resin coating from the pharmaceutical to release the active agent within the cellular interstices by radiofrequency heating the microcapsules above the melt temperature of the encapsulating resin.

6. A method according to claim 5 wherein the heating is of a small organ or segment of the body capable of having its temperature elevated to a level of at least 40° C. for a period of time sufficient to elevate the temperature of the microcapsules above the melting point of their encapsulating resin.

7. A method according to claim 5 wherein the polymeric encapsulating resin coating removed is an acrylate polymer and the biologically active pharmaceutical is a cytotoxic cancericidal composition.

8. A method for treatment of tumors of mammals which comprises:
   (a) preheating the tumor to be treated and elevating its temperature above body temperature,
   (b) administering a therapeutic dose of a tumoricidal agent encapsulated with a coating having a melting point higher than the temperature of the surrounding nontumor body tissue and within the elevated temperature range of the tumor into the interstices of the tumor and
   (c) activating the tumoricidal agent by heating the same within the tumor interstices to a temperature above the melting point of its encapsulated coating.

9. A method for the administration of biologically active pharmaceuticals into a neoplasm of a mammal to reduce systemic side effects thereof which comprises:
   (a) introducing intratumorally and extarcellularly into the interstices of the neoplasm within the segment of the mammal to be treated a therapeutic dose of microcapsules of a biologically active pharmaceutical substrate which has been precoated with a releasable encapsulating coating of lauric acid or esters of lauric acid which have a melting point range extending from 40°–46° C. and which will until the coating is removed remain substantially inert biologically;
   (b) removing this coating from the pharmaceutical substrate to release the active agent within the interstices by radiofrequency heating of the microcapsules above the melt temperature of the coating.

* * * * *